US010889792B2

(12) United States Patent
Griffin et al.

(10) Patent No.: US 10,889,792 B2
(45) Date of Patent: Jan. 12, 2021

(54) CELL EXPANSION VESSEL SYSTEMS AND METHODS

(71) Applicant: Global Life Sciences Solutions USA LLC, Marlborough, MA (US)

(72) Inventors: Weston Blaine Griffin, Niskayuna, NY (US); Xiaohua Zhang, Niskayuna, NY (US); Reginald Donovan Smith, Schenectady, NY (US); Vandana Keskar, Schenectady, NY (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 0 days.

(21) Appl. No.: 15/893,336

(22) Filed: Feb. 9, 2018

(65) Prior Publication Data

US 2019/0249130 A1 Aug. 15, 2019

(51) Int. Cl.
| | |
|---|---|
| *C12M 1/00* | (2006.01) |
| *C12M 1/04* | (2006.01) |
| *C12N 5/0783* | (2010.01) |
| *C12M 1/34* | (2006.01) |
| *C12M 1/12* | (2006.01) |
| *C12M 1/26* | (2006.01) |
| *C12M 1/24* | (2006.01) |

(52) U.S. Cl.
CPC ............ *C12M 29/04* (2013.01); *C12M 23/08* (2013.01); *C12M 23/24* (2013.01); *C12M 25/02* (2013.01); *C12M 25/06* (2013.01); *C12M 29/18* (2013.01); *C12M 29/26* (2013.01); *C12M 33/00* (2013.01); *C12M 41/46* (2013.01); *C12N 5/0636* (2013.01)

(58) Field of Classification Search
CPC ...... C12M 29/04; C12M 23/08; C12M 29/18; C12M 23/24; C12M 41/46; C12M 25/06; C12M 29/26; C12M 33/00; C12M 25/02; C12N 5/0636
See application file for complete search history.

(56) References Cited

U.S. PATENT DOCUMENTS

| | | |
|---|---|---|
| 4,143,764 A | 3/1979 | Moss |
| 5,449,617 A | 9/1995 | Falkenberg et al. |
| 5,686,304 A | 11/1997 | Codner et al. |
| 5,707,869 A | 1/1998 | Wolf et al. |
| 6,410,309 B1 | 6/2002 | Barbera-Guillem et al. |
| 6,455,310 B1 | 9/2002 | Barbera-Guillem |
| 6,479,252 B1 | 11/2002 | Barbera-Guillem et al. |
| 6,821,772 B2 | 11/2004 | Barbera-Guillem et al. |
| 6,900,055 B1 | 5/2005 | Fuller et al. |
| 7,745,209 B2 | 6/2010 | Martin et al. |
| 7,964,392 B2 | 6/2011 | Hatano et al. |
| 8,158,427 B2 | 4/2012 | Wilson et al. |
| 8,492,140 B2 | 7/2013 | Smith et al. |
| 8,956,860 B2 | 2/2015 | Vera et al. |
| 9,110,114 B2 | 8/2015 | Nezuka |
| 9,255,243 B2 | 2/2016 | Wilson et al. |
| 9,315,774 B2 | 4/2016 | Knaus et al. |
| 9,441,192 B2 | 9/2016 | Wilson et al. |
| 9,732,317 B2 | 8/2017 | Wilson et al. |
| 2008/0000902 A1 | 1/2008 | Holbrook et al. |
| 2009/0037031 A1 | 2/2009 | George et al. |
| 2010/0291534 A1 | 11/2010 | Higuchi et al. |

(Continued)

FOREIGN PATENT DOCUMENTS

| | | |
|---|---|---|
| EP | 0950432 A1 | 10/1999 |
| EP | 1944359 A1 | 7/2008 |

(Continued)

OTHER PUBLICATIONS

Schwarz, Ray P., et al.; "Cell Culture for Three-Dimensional Modeling in Rotating-Wall Vessels: An Application of Simulated Microgravity", Journal of tissue culture methods, vol. 14, Issue 02, pp. 51-57, Jun. 1992.

Hung, Paul J., et al.; "A Novel High Aspect Ratio Microfluidic Design to Provide a Stable and Uniform Microenvironment for cell Growth in a High Throughput Mammalian Cell Culture Array", Link of General Homepage, vol. 05, pp. 44-48, Nov. 2, 2004.

Shojaosadati, Seyed Abbas, et al.; "Recent Advances in High Cell Density Cultivation for Production of Recombinant Protein", Iranian Journal of Biotechnology, vol. 06, Issue 02, pp. 63-84, 2008.

International Search Report for PCT/EP Application No. 2019/053210, dated May 22, 2019 (13 pages).

International Search Report for PCT/EP Application No. 2019/053209, dated May 13, 2019 (14 pages).

(Continued)

*Primary Examiner* — Taeyoon Kim
(74) *Attorney, Agent, or Firm* — Eversheds Sutherland (US) LLP

(57) ABSTRACT

A method includes introducing a suspension including cells suspended in a cell culture medium through a feed port or a drain port into a cavity of a cell culture vessel, the suspension being in an amount sufficient to cover a gas permeable, liquid impermeable membrane positioned at a bottom of the cell culture vessel, the feed port being disposed through a surface of the cell culture vessel and configured to permit additional cell culture medium into the cavity, and the drain port being disposed through the surface of the cell culture vessel and configured to permit removal of the cells, cell culture medium, and used cell culture medium from the cavity, allowing the cells to settle on the gas permeable, liquid impermeable membrane by gravity, removing the used cell culture medium through the drain port and introducing the additional cell culture medium through the feed port such that a constant volume is maintained in the cell culture vessel until the cells expand to a desired cell density, wherein the removing and introducing are performed subsequent to allowing the cells to settle on the gas permeable, liquid impermeable membrane, resuspending the cells in the cell culture medium in the cell culture vessel, wherein the resuspending is performed after the desired cell density is attained, and removing the resuspended cells and the cell culture medium through the drain port.

16 Claims, 5 Drawing Sheets

(56) References Cited

U.S. PATENT DOCUMENTS

| | | | |
|---|---|---|---|
| 2015/0329815 A1* | 11/2015 | Wilson | C12M 23/08 |
| | | | 435/325 |
| 2016/0319233 A1 | 11/2016 | Shimase et al. | |
| 2016/0340633 A1* | 11/2016 | Davis | C12M 27/16 |
| 2017/0058242 A1 | 3/2017 | Martin et al. | |

FOREIGN PATENT DOCUMENTS

| | | |
|---|---|---|
| EP | 2589652 A1 | 5/2013 |
| WO | 97/24144 A1 | 7/1997 |
| WO | 02/102965 A2 | 12/2002 |
| WO | 03/087292 A2 | 10/2003 |
| WO | 2005/009126 A1 | 2/2005 |
| WO | 2008/109200 A1 | 9/2008 |
| WO | 2009/112952 A2 | 9/2009 |
| WO | 2010/062599 A1 | 6/2010 |
| WO | 2010/080032 A2 | 7/2010 |
| WO | 2015/042450 A1 | 3/2015 |
| WO | 2016/007216 A1 | 1/2016 |
| WO | 2016/100227 A1 | 6/2016 |
| WO | 2016/107788 A1 | 7/2016 |
| WO | 2016/118780 A1 | 7/2016 |
| WO | 2016/161174 A1 | 10/2016 |
| WO | 2016/168687 A1 | 10/2016 |
| WO | 2016/185221 A1 | 11/2016 |
| WO | 2017/032829 A1 | 3/2017 |
| WO | 2017/109083 A1 | 6/2017 |
| WO | 2017/144440 A2 | 8/2017 |
| WO | 2019/046766 A2 | 3/2019 |

OTHER PUBLICATIONS

International Search Report for PCT/EP Application No. 2019/053212, dated May 27, 2019 (9 pages).

International Search Report for PCT/EP Application No. 2019/053208, dated May 21, 2019 (13 pages).

International Search Report for PCT/EP Application No. 2019/053206, dated May 15, 2019 (12 pages).

International Search Report for PCT/EP Application No. 2019/053211, dated May 29, 2019 (10 pages).

International Search Report for PCT/EP Application No. 2019/053205, dated Apr. 30, 2019 (12 pages).

International Search Report for PCT/EP Application No. 2019/053207, dated May 3, 2019 (13 pages).

* cited by examiner

CELL EXPANSION VESSEL SYSTEMS AND METHODS

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The subject matter disclosed herein relates to cell expansion vessel systems and methods. More specifically, embodiments of the present disclosure relate to a static cell culture vessel that facilitate increased high density cell expansion through perfusion.

Various medical therapies involve the culture and expansion of cells to increase cell density for downstream therapeutic processes. For example, chimeric antigen receptor cell therapy (e.g., CAR-T) involves extraction of white blood cells from a donor and genetically engineering the cells in such a way that enables the cells to identify and attack malignant cells. The engineered cells are then transferred to expansion vessels to allow the cells to proliferate to achieve a particular target dosage. Typical cell culture and/or expansion devices may permit expansion and culture of the engineered cells. However, typical cell culture and/or expansion devices may be bulky and may not produce a relatively high density cell culture. Further, typical cell culture and/or expansion devices may not allow for reduction of impurities in the cell culture without further washing of the cells, conventionally accomplished through use of a designated washing device.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a method includes introducing a suspension including cells suspended in a cell culture medium through at least a feed port or a drain port into a cavity of a cell culture vessel, the suspension being in an amount sufficient to cover a gas permeable, liquid impermeable membrane positioned at a bottom of the cell culture vessel, the feed port being configured to permit additional cell culture medium into the cavity, and the drain port being configured to permit removal of the cells, cell culture medium, and used cell culture medium from the cavity, allowing the cells to settle on the gas permeable, liquid impermeable membrane by gravity, removing the used cell culture medium through the drain port and introducing the additional cell culture medium through the feed port such that a constant volume is maintained in the cell culture vessel until the cells expand to a desired cell density, wherein the removing and introducing are performed subsequent to allowing the cells to settle on the gas permeable, liquid impermeable membrane, resuspending the cells in the cell culture medium in the cell culture vessel, wherein the resuspending is performed after the desired cell density is attained, and removing the resuspended cells and the cell culture medium through the drain port.

In a second embodiment, a method includes introducing a suspension including cells suspended in a cell culture medium through at least a feed port or a drain port into a cavity of a cell culture vessel, the suspension being in an amount sufficient to cover a gas permeable, liquid impermeable membrane positioned at a bottom of the cell culture vessel, the feed port being disposed through a surface of the cell culture vessel and configured to permit additional cell culture medium into the cavity, and the drain port being disposed through the surface of the cell culture vessel and configured to permit removal of the cells, cell culture medium, and used cell culture medium from the cavity, allowing the cells to settle on the gas permeable, liquid impermeable membrane by gravity, perfusing the cells with the cell culture medium, wherein the perfusing includes introducing the additional cell culture medium through the feed port while simultaneously or nearly simultaneously removing the used cell culture medium from the cell culture vessel via the drain port while maintaining a constant volume within the cell culture vessel until the cells expand to a desired cell density, wherein the perfusing is performed subsequent to allowing the cells to settle on the gas permeable, liquid impermeable membrane, sampling the cells via the drain port to determine whether the desired cell density is reached, repeating, upon determining that the desired cell density has not been reached, the perfusing of the cells until the desired cell density is reached, resuspending the cells in the cell culture medium in the cell culture vessel, wherein the resuspending is performed after the desired cell density is reached, and removing the resuspended cells and the cell culture medium through the drain port.

In a third embodiment, a cell culture vessel for expansion of a cell density includes a bottom plate including a grid surface configured to provide support and gas exchange, a vessel body coupled to the bottom plate, wherein the vessel body includes a rigid concave structure, a cavity formed by the vessel body and the bottom plate, a gas-permeable, liquid impermeable membrane disposed above the bottom plate within the cavity, a feeding port disposed through a surface of the vessel body, wherein the feeding port is configured to permit addition of cell culture medium into the cavity, and a drain port disposed through a wall of the vessel body, wherein the drain port is configured to permit removal of used cell culture medium from the cavity, wherein the cell culture vessel is configured to hold a suspension including cells suspended in the cell culture medium, wherein the cell culture medium within the cell culture vessel comprises a ratio of cell culture medium volume per surface area of the gas permeable, liquid impermeable membrane that is below a predetermined threshold value.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
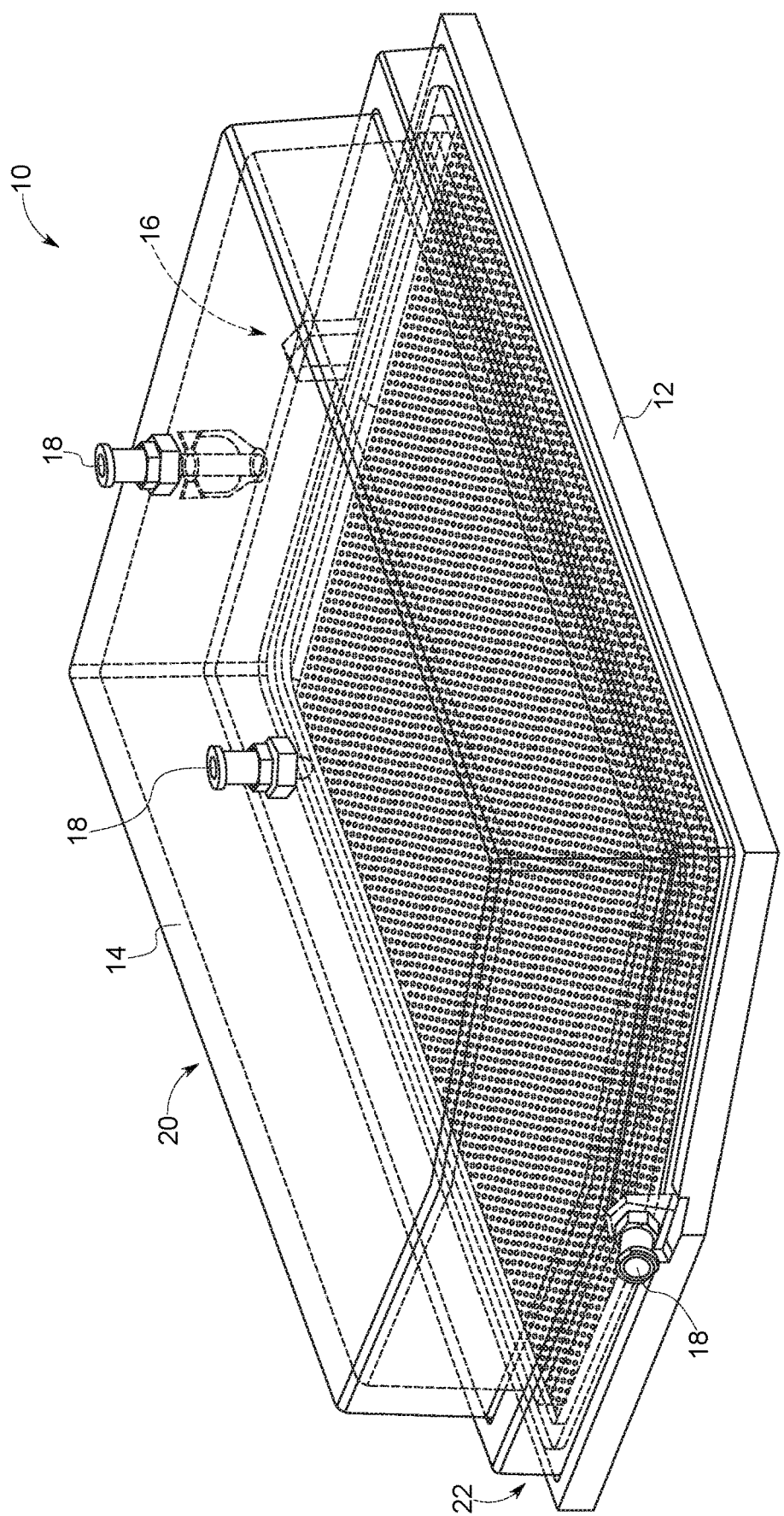
FIG. 1 is a perspective view of an embodiment of a cell culture vessel, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

CAR-T involves extracting white blood cells from a donor and genetically engineering them in such a way so they can identify and attack malignant cells. Typical CAR-T upstream processes include enrichment of peripheral blood mononuclear cells (PBMCs), isolation of the T-cells, activation, and transduction before a final expansion phase. For this latter phase, engineered CAR-T cells are transferred to expansion devices to allow them to proliferate to meet a dose target. Cell culturing devices for CAR-T cells include a WAVE bioreactor, which constantly agitates the cell culture by creating a wave motion, while actively flowing gas and the option of exchanging cell culture media through perfusion. Static devices may also be used, such as static, gas permeable bags which allow gas exchange through the film. These bags only support up to ~3.5 MM/mL or about 1 MM/cm$^2$ cell culture, similar to static T-flasks. Other cell culture devices may include static devices having a silicone membrane on the bottom surface. The high gas permeability of the silicone membrane permits cell culture density up to 30 MM/cm$^2$. However, the static devices do not support media exchange through perfusion.

Provided herein are cell culture vessels that may be used to achieve high cell density for use in medical therapeutics or other processes. The disclosed cell culture vessels and methods may include a gas permeable membrane to provide oxygen to the cell culture. The cell culture vessel may permit filterless or filter-free perfusion to both provide the cell culture with the medium needed to support cell growth and remove impurities. Such perfusion as provided herein may in turn lead to increased cell density cell culture compared to typical cell culture and/or cell expansion vessels. Additionally, the use of perfusion to replace used growth medium while removing the used medium in the cell culture vessel allows cells to proliferate in relatively lower volumes of growth medium, which in turn allows the overall profile of the cell culture vessel to be a low-profile structure. Further in conjunction with a low-profile cell culture vessel, the cell culture vessel may include fewer ports than typical cell culture and/or cell expansion devices. For example, the cell culture vessel as provided herein may combine the ports for media removal and cell removal into a single drain port. The cell culture vessel also provides built-in impurity reduction capability without necessarily needing steps for further washing. The cell culture vessel may also be used to concentrate the cell culture. Further, the cell culture vessel may be a rigid vessel which, with agitation, may encourage a homogenous mixture within the cell culture vessel for use in collecting online samples.

The disclosed techniques provide an automated cell culturing device that can support higher cell density through filter-free perfusion in a compact format, such as a low profile static device, relative to conventional cell culturing devices. The disclosed cell culturing devices also permits the user to take online samples for monitoring cell growth throughout the culture period. The homogeneity of the samples is promoted by the design of the device.

The disclosed cell culturing device not only supports the cell growth by providing fresh medium, but also removes impurities at the same time. The advantage of such a device is that the cell culturing techniques may be performed without transfer of the cell culture to a designated cell washing device for washing out the impurities. The disclosed device provides just the right amount of nutrients for supporting cell growth (anything more than that would be unnecessary from supporting cell growth point of view), while being able to provide enough wash through perfusion. The perfusion-based wash may have the general wash factor of one log with continuous perfusion at a rate that exchanges about 2.3× volumes. For example, if the vessel has 450 mL volume, one volume exchange per day would add 450 mL of fresh medium and remove 450 mL of the used existing medium from the vessel, and the effective impurity reduction from the original vessel volume would be 1 log in a little over 2 days. It would be 2 log if the perfusion continues for about 4.5 days, etc. At the end of cell culture, the volume may be maintained the same, i.e. 450 ml, with desired impurity level without further washing using the purification scheme provided.

FIG. 1 is a perspective view of an embodiment of a cell culture vessel 10. The cell culture vessel 10 may be used for cell culture, cell processing, and/or cell expansion to increase cell density for use in medical therapeutics or other processes. While the cell culture vessel 10 may be disclosed herein as being used in conjunction with particular cell types, it should be understood that the cell culture vessel may be used for expansion of any suitable cell type. Further, the disclosed techniques may be used in conjunction with adherent cells, i.e., cells that adhere to and/or proliferate on a cell expansion surface.

The cell culture vessel may include a bottom plate 12. The bottom plate 12 may be a rigid structure to support a cell culture. However, the bottom plate 12 may be a non-solid plate (e.g., may be open and/or porous) to permit oxygen to be provided to the cell culture, as discussed in greater detail with reference to FIG. 2. In the illustrated embodiment, the bottom plate 12 is a rectangular, or almost rectangular, shape. In other embodiments, the bottom plate 12 may be any other shape that may enable a low-profile vessel and/or may maximize space in the location that the cell culture vessel may be utilized or stored.

The cell culture vessel 10 may further include a vessel body 14 that may couple with the bottom plate 12. The vessel body 14 may have a rigid concave structure that, when coupled to the bottom plate 12, forms a cavity 16 of the cell culture vessel 10. The vessel body 14 may have a perimeter shape that is similar to the perimeter shape of the bottom plate 12 such that the vessel body 14 and the bottom plate 12 may be coupled. Additionally, as in the illustrated embodiment, the vessel body 14 may be made of a transparent or translucent material that may enable visual inspection of the cell culture and/or may enable light to enter the cell culture vessel 10. The cavity 16 formed by the bottom plate 12 and the vessel body 14 may contain a cell medium and the cell culture during use of the cell culture vessel 10 for cell culture and/or cell expansion.

The cell culture vessel 10 may include multiple ports 18 through the vessel body 14 that may enable communication between the cavity 16 and the outside of the cell culture vessel 10 for certain processes related to the cell culture and/or cell expansion, such as media input and waste removal. The ports 18 may be disposed at any location in the vessel body 14, including through a top surface 20 and/or any of the sides 22 of the vessel body, as in the illustrated embodiment. As will be discussed in greater detail herein, the structure of the cell culture vessel 10, including the quantity and position of the various ports 18, may enable the cell culture vessel 10 to be used to support high cell density expansion.

Figure 2:
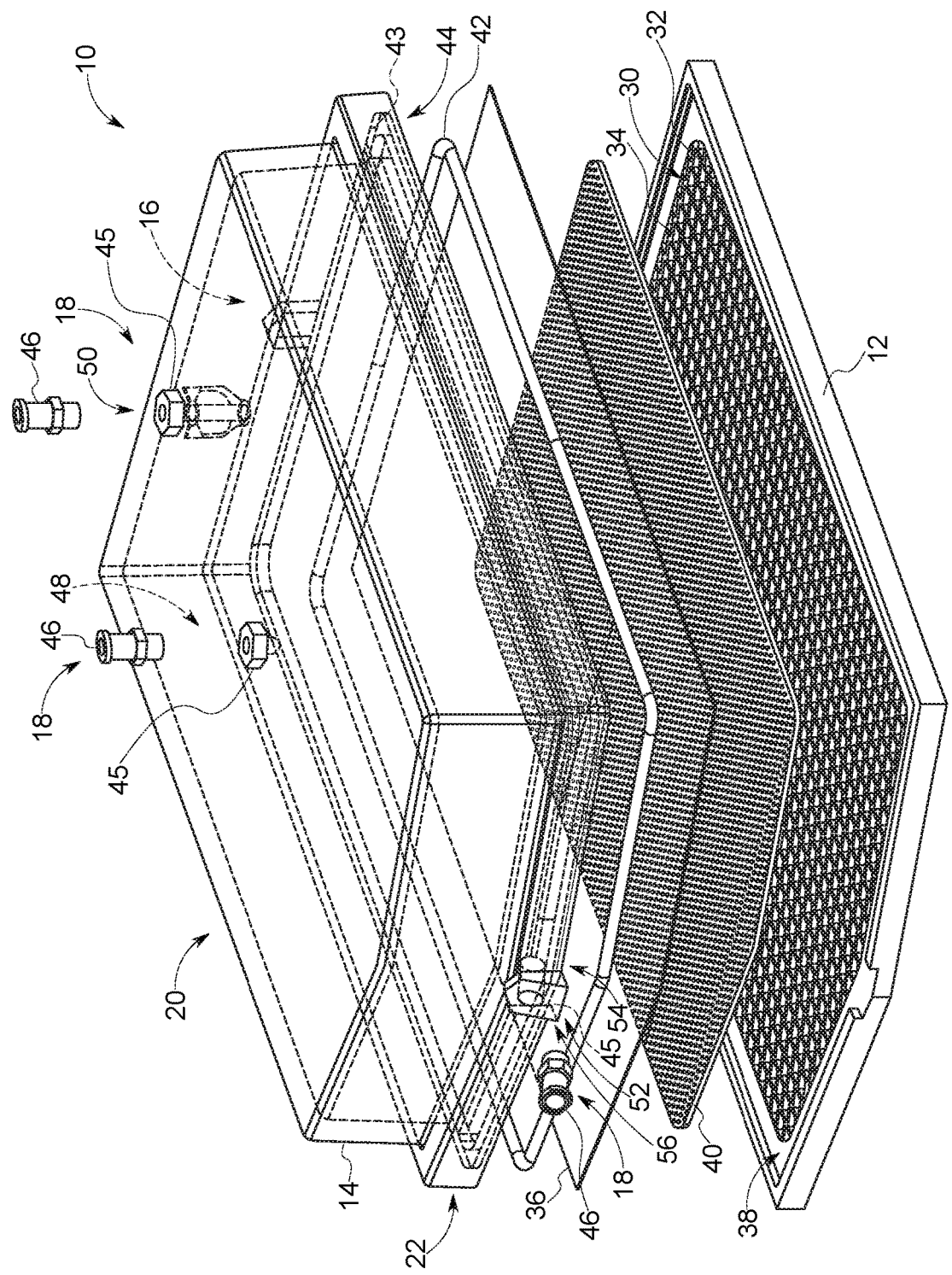
FIG. 2 is an exploded view of an embodiment of the cell culture vessel of FIG. 1, in accordance with aspects of the present disclosure.

FIG. 2 is an exploded view of an embodiment of the cell culture vessel 10. The bottom plate 12 of the cell culture vessel 10 may be the bottom or support of the cell culture vessel 10. As previously discussed, the bottom plate 12 may be formed of a non-solid structure. In the illustrated embodiment, the bottom plate 12 contains a grid 30 that may be structurally rigid while further providing opening to enable free gas exchange through the bottom plate 12 to the cavity 16 containing the cell culture. The grid 30 may include multiple holes 32 having solid crossbars 34 between each hole 32 of the grid 30. Thus, the holes 32 may provide openings for gas exchange, and the crossbars 34 may provide structural support for other structure and the cell culture within the cavity 16 of the cell culture vessel 10.

To provide further support for the cell culture within the cavity 16 of the cell culture vessel 10, the cell culture vessel 10 may include a membrane 36 that may be disposed above a top surface 38 of the bottom plate 12. The membrane 36 may be a gas permeable, liquid impermeable membrane. The membrane 36 may also be selected having properties enabling high gas permeability, high gas transfer rates, and/or high permeance to oxygen and carbon dioxide. Therefore, the membrane 36 may support high cell densities (e.g., up to about 35 MM/cm$^2$) within the cavity 16. The gas permeability feature of the membrane may enable the free gas exchange to support the cell culture and/or cell expansion. As such, the membrane 36 may be a cell culture and/or cell expansion surface. The membrane 36 may have a relatively small thickness (e.g., 0.010 inches or 0.02 cm), which may permit the membrane 36 to be gas permeable.

Further, the membrane 36 may be formed from a gas permeable material, such as silicone or other gas permeable material.

Flatness of the membrane 36 may increase the surface area for the cell culture to settle on for expansion. To enable the membrane 36 to remain flat during use of the cell culture vessel 10, a mesh sheet 40 may be disposed between the bottom plate 12 and the membrane 36. The mesh sheet 40 may provide structural support to the membrane 36, such that the membrane 36 may remain planar and may not sag or distort under the weight of the cell culture and/or any cell medium added to the cell culture vessel 10 for cell culture and/or cell expansion. Further, the mesh characteristic of the mesh sheet 40 may enable support of the membrane 36, while still enabling free gas exchange between the cavity 16 of the cell culture vessel 10 and outside of the cell culture vessel 10. The mesh sheet may be a polyester mesh, or any other type of mesh that may provide support to the membrane and enable free gas exchange.

As previously discussed, the vessel body 14 may be coupled to the bottom plate 12 to form the cavity 16 of the cell culture vessel 10. As such, the mesh sheet 40 and the membrane 36 may be disposed within, or at least partially within, the cavity 16. An O-ring 42 may be used to seal the cell culture vessel 10 when the vessel body 14 is coupled to the bottom plate 12. In an embodiment, the O-ring 42 may be a biocompatible O-Ring (Size 173, Soft Viton® Fluoroelastomer O-Ring). The O-ring 42 may fit within a groove 43 in a bottom surface 44 of the vessel body 14. The groove 43 may be along the edge in the bottom surface 44 of the vessel body 14. As such, the O-ring 42 may be compressed within the groove 43 and against the top surface 38 of the membrane 36 and/or the bottom plate 12. Such compression of the O-ring 42 may seal the cell culture vessel 10 without any chemical or epoxy bonding. As the cell culture vessel 10 may be used for cell culture and/or cell expansion of biological cells, the O-ring 42 may be biocompatible, autoclavable, and/or gamma radiation stable.

As discussed above, the cell culture vessel 10 may include multiple ports 18. The ports 18 may be disposed through the vessel body 14 and may enable communication between the cavity 16 and the outside of the cell culture vessel 10 for certain processes related to the cell culture and/or cell expansion, such as media input and waste removal. Each port 18 may include an opening 45 and a respective fitting or tubing 46 (e.g., a luer fitting). In the illustrated embodiment, the cell culture vessel 10 contains three ports 18 through the vessel body 14, including an air filter 48, a feeding port 50, and a drain port 52.

The air filter 48 may further provide gas exchange between the cavity 16 and outside of the cell culture vessel 10 for use by the cell culture for expansion. Further, the air filter 48 may help maintain atmospheric pressure within the cavity 16 to provide an environment within the cavity 16 for cell culture and/or cell expansion. The air filter 48 may be disposed through the top surface 20 of the vessel body 14, as in the illustrated embodiment, or at any other position about the vessel body 14. A central position through the top surface 20 of the vessel body 14 may help prevent wetting of the air filter 48 during mixing of the cell culture through tilting of the cell culture vessel 10, as discussed in greater detail below.

Each element of the cell culture vessel 10, including the bottom plate 12, the vessel body 14, the ports 18, the membrane 36, the mesh sheet 40, and the O-ring 42, may be made from material that are biocompatible, autoclavable, and gamma radiation stable. As such, each element, and the cell culture vessel 10 as a whole unit, may be used for expansion of biological cells, and/or for other processes of the cell manufacturing process.

The cell culture vessel 10 may enable cell culture and/or cell expansion via perfusion, which may provide nutrients necessary for supporting cell growth and may reduce impurities in the cell culture. Continuous perfusion is the addition of a fresh media supply to the growing cell culture with simultaneous removal of spent media (e.g., used media). Some of the ports 18 may be used for the perfusion process, including the feeding port 50 and the drain port 52. The feeding port 50 may enable communication between the cavity 16 and the outside of the cell culture vessel 10 and may be used to add a fresh medium into the cell culture vessel 10. In some embodiments, the feeding port 50 may be disposed in and extend through the vessel body 14 at any location above the surface of the cell culture and medium within the cell culture vessel 10. In some embodiments, the feeding port 50 may be disposed such that it contacts or extends through the surface of the cell culture and medium within the cell culture vessel 10.

The drain port 52 may be disposed at any location that is fully or partially submerged under the surface of the cell culture and the medium within the cell culture vessel 10. For example, the drain port 52 may be a nearly lateral port disposed through one of the sides 22 of the vessel body 14. In some embodiments, the drain port 52 may be disposed such that the drain port 52 does not reach to the bottom of the cavity 16 (e.g., the membrane 36). In some embodiments, the drain port 52 may reach the bottom of the cavity 16. The drain port 52 may be a dual functionality port. As such, the drain port 52 may be used to pull the perfusion media out of the cavity 16 of the cell culture vessel 10 to facilitate perfusion of the cell culture. Further, the drain port 52 may also be used to remove the cells of the cell culture. As noted above, in some embodiments, the drain port 52 may not reach the bottom surface of the cavity 16 of the cell culture vessel 10. For example, the drain port 52 may be located 0.5 cm away from the membrane 36. Therefore, in a static planar position, the drain port 52 may be used to remove the spent cell culture medium without pulling out the cells of the cell culture because the cells may settle to the membrane 36 (e.g., the cell expansion surface) via gravity. Thus, in the static planar position, the drain port 52 may facilitate the perfusion process and may enable an increase in the cell density of the growing cell culture within the cell culture vessel 10. When cells are desired to be removed from the cavity 16, for example during harvest of the cell culture, to minimize the hold-up volume, the cell culture vessel may be tilted toward the drain port 52 providing access to the cells for cell removal.

Additionally, the drain port 52 may not include a filter and thus, the perfusion process may be filter-free. As such, there may be no physical blockage of the cells from entering the drain port 52 when the drain port 52 is used for media removal. Further, the drain port 52 may be slanted such that although the drain port 52 is disposed laterally through the side 22 of the vessel body 14, the drain port 52 may be slanted toward the membrane 36 and the bottom plate 12. The slanted feature of the drain port 52 may enable the drain port 52 to be positioned relatively low on the vessel body 14 closer to the membrane surface 36, while minimizing interference with the O-ring 42 and the groove 43 to help maintain sealing of the cell culture vessel 10 when in use. Further, in some embodiments, the slanted feature of the drain port 52 may lower the velocity of the fluid flow through the drain port 52 when used medium is removed.

Additionally, the port diameter in conjunction with fluid flow rate out of the drain port 52 may be such that an inhaling velocity through the drain port 52 used to pull the media out of the cavity 16 may minimize suction force on individual cells adjacent to the drain port 52 such that the force is lower than the gravitational force pulling the cells toward the membrane 36 In an embodiment, a perfusion flow rate is set at 1.2 ml/min, the diameter of the drain port 52, at the suction head, is 0.15" (about 0.4 cm); assuming uniform flow into the drain port, the velocity at the suction head is 0.88 mm/s. The drain port 52 is located 0.5 cm away from the bottom surface. With 1.2 mL/min flow rate, the medium being pulled out from the drain port 52 has only 1.6e5/mL cell concentration (the starting homogeneous cell culture had a concentration of 6.2e6/mL cell) or <2.5% of the culture concentration, starting after 3 hours of settling time from homogeneous cell culture. This cell concentration further drops to 5.6e4 cells/mL or <0.9% of the culture concentration, starting after 4 hours of settling time from homogeneous cell culture.

Therefore, as discussed above, the drain port 52 may be used to remove the perfusion medium to facilitate perfusion of the cell culture without substantially removing the cells of the cell culture. As the settling time of the cells increases, a cell concentration of the removed media may decrease into an immeasurable range facilitated by the position of the drain port 52. Further, the position of the interior opening 55 may be changed to change the recommended cell settling time. Positions closer to the membrane 36 may be associated with longer settling times, while positions at or nearer to a top of the medium are associated with shorter settling times, because cells will settle and be first depleted from the top of the growth medium.

As previously discussed, the drain port 52 may be used not only for removal of the used media during the perfusion process, but may also be used to remove cells of the cell culture from the cavity 16, for example during harvest of the cell culture. To facilitate greater removal of the used perfusion medium and removal of cells, the vessel body may include an angled side 54. The angled side 54 may have a V-shape, such that the angled side 54 of the vessel body 14 comes to a point 56. The point 56 of the angled side 54 of the vessel body 14 may be located such that the drain port 52 through the vessel body 14 is disposed near the point 56 when the vessel body 14 coupled to the bottom plate 12. The angled side 54 and the point 56 may enable greater drainage of the media and/or the cells of the cell culture when the cell culture vessel 10 is tilted toward the drain port 52, e.g., at a 5 degree angle.

Figure 3:
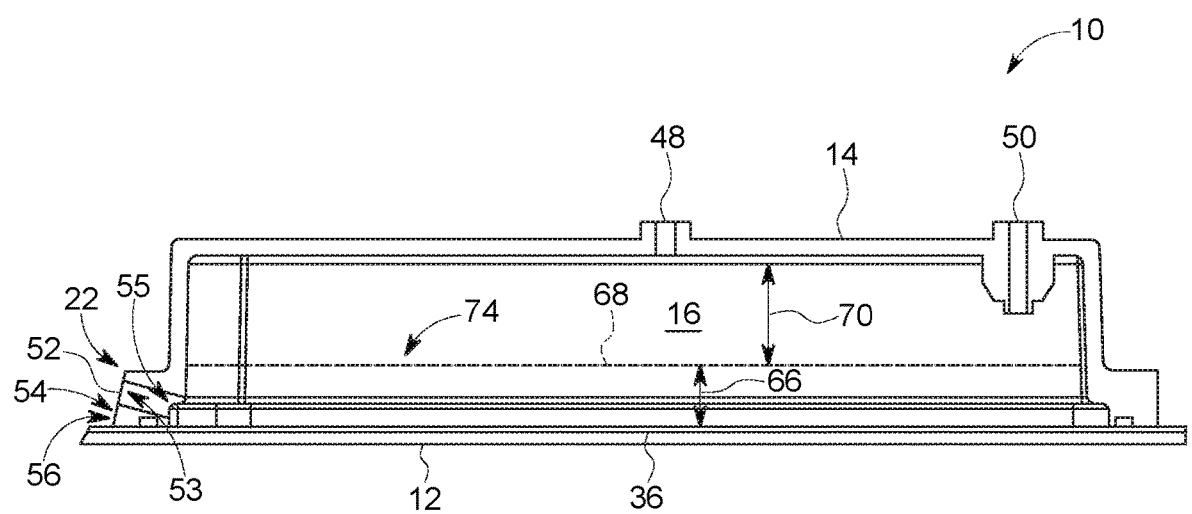
FIG. 3 is a cross-sectional view of an embodiment of the cell culture vessel of FIG. 1, in accordance with aspects of the present disclosure.

The use of perfusion to grow the cells facilitated by the positions of the feeding port 50 and the drain port 52 may enable a low media height within the cavity 16, as discussed in greater detail with reference to FIG. 3. A relatively low media height within the cavity 16 may enable the cell culture vessel 10 to be a relatively low-profile vessel, while enabling an increase in the maximum achievable cell density. Further, the use of perfusion with the cell culture vessel 10 may support cell growth by providing fresh medium to the cells within the cavity 16, but also enable removal of impurities in the cell culture, such that additional cell washing in a separate device may not be needed once a particular cell density goal is reached within the cell culture vessel 10. For example, through the filter-free perfusion, the cell culture vessel 10 may provide fresh medium and reduce impurities within the cell culture at a rate of a full volume exchange per day (e.g., resulting in an impurity reduction at a rate of approximately 1 log per 2.3 days). Therefore, the structure of the cell culture vessel 10 may enable the use of perfusion for growing the cell culture within the cell culture vessel 10, which may thus enable expansion of the cell culture to a high target density with a reduced impurity level.

To facilitate a low-profile structure of the cell culture vessel 10, a relatively low media height within the cavity 16 may be maintained. FIG. 3 is a cross-sectional view of the cell culture vessel 10 illustrating a height 66 of cell media 68 within the cell culture vessel 10. As previously discussed, the vessel body 14 may be coupled to the bottom plate 12 to form the cavity 16 within which expansion of the cell culture may be achieved through perfusion. As such, replacement or fresh medium 68 may be provided for cell growth through the feeding port 50 disposed through the vessel body 14, and existing or used medium 68 may be removed through the drain port 52 disposed through the side 22 of the vessel body 14. The perfusion process may facilitate relatively low medium height 66 of the medium 68 within the cavity 16 of the cell culture vessel 10. The relatively low height 66 of the perfusion medium 68 within the cavity 16 may enable the cell culture vessel 10 to be a low-profile structure, which thus, may enable a compact cell manufacturing system as a whole.

The height 66 of the perfusion medium 68 within the cavity 16 of the cell culture vessel 10 may be between 0.3 cm and 2 cm, and the height of the head room 70, i.e., a gap formed between the medium 68 and the top surface 20 of the vessel body 14 in the cavity 16, may be approximately 2 cm. Thus, there may be less than 2 mL of media per $cm^2$ and less than 4 mL of total volume per $cm^2$, including the media, the cell culture, and headspace. A relatively low media height 66 may enable a ratio of media volume to surface area of the membrane 36 to be below a certain value. As such, the ratio of the medium volume to the membrane surface area may be below a threshold level, or within a desirable range, facilitated by the use of perfusion to grow the cells of the cell culture. The threshold level may be a ratio between 0.3-2.0. The low ratio medium volume to membrane surface area may enable the cell culture vessel 10 to have a low-profile or compact structure, while still permitting a high cell density cell culture to be achieved.

As previously discussed, the dual functionality drain port 52 may be disposed through the vessel body 14 such that it is fully or partially submerged under a surface 74 of the medium 68 within the cell culture vessel 10. In some embodiments, the drain port 52 may be disposed such that the drain port 52 reaches to the bottom of the cavity 16 (e.g., the membrane 36). Positioning of the drain port 52 may facilitate media and impurity removal from the cell culture within the cavity 16, without removal of the cells until such removal is desired, for example harvesting. The filter-free drain port 52, along with the feeding port 50, may permit the use of perfusion to provide the growth medium 68 to the cells for cell expansion, and to remove the used medium 68 and other impurities or byproducts. The position of the feeding port 50 and the dual functioning drain port 52 about the vessel body 14 facilitates a configuration in which the height 66 of the medium within the cavity 16 to be maintained at a relatively low level and thus, permit the cell culture vessel 10 to be a relatively low-profile vessel, while still permitting generation of a high density cell culture.

Figure 4:
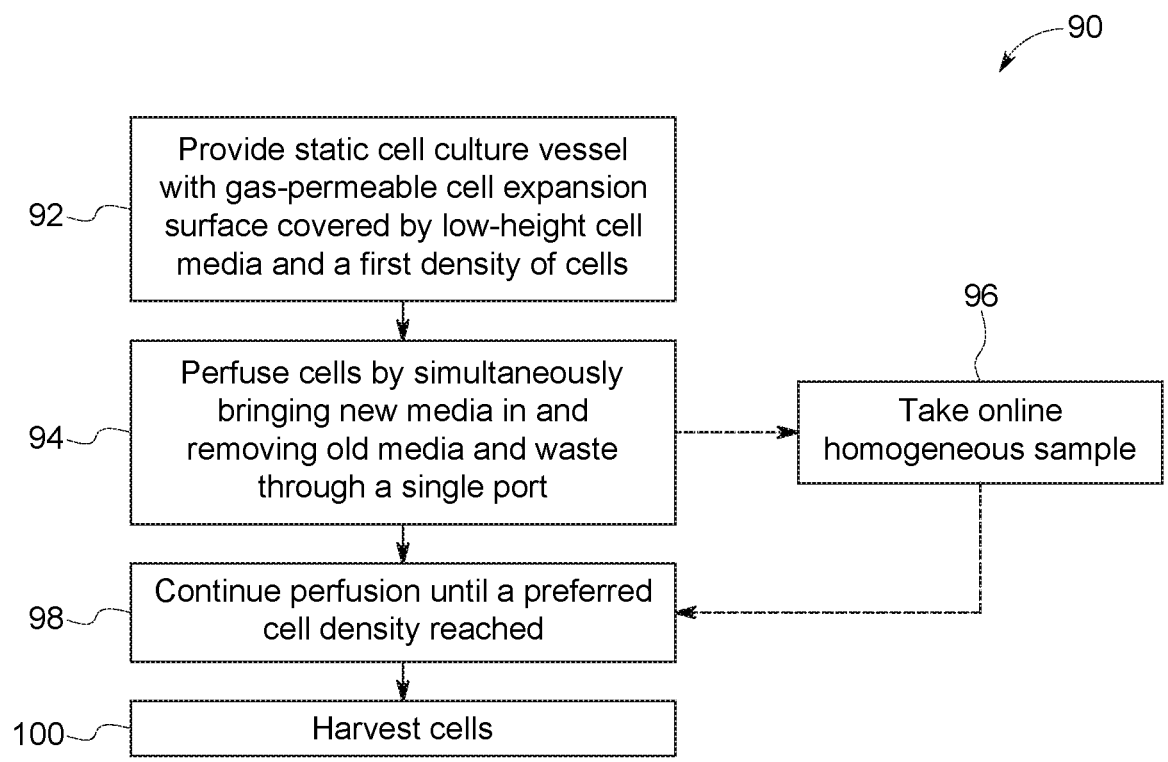
FIG. 4 is a flow diagram of an embodiment of a method cell expansion using the cell culture vessel of FIG. 1, in accordance with aspects of the present disclosure.

With the foregoing in mind, FIG. 4 illustrates a flow chart of a method 90 for cell expansion using the cell culture vessel 10. At block 92, the static cell culture vessel 10 may be provided. The cell culture vessel 10 may include a gas permeable membrane 36 (e.g., cell expansion surface) and cells at a first density. As previously discussed, the height 66 of the medium 68 within the cavity 16 of the cell culture vessel 10 may be relatively low, and in certain embodiments, may be between 0.3 cm and 2 cm relative to the membrane 36 (e.g. cell expansion surface). Further, the medium volume per surface area of the membrane 36 may be below a certain value, thus enabling the cell culture vessel to have a low-profile and compact structure. Before beginning perfusion of the cell culture, the cells may be permitted to settle to the membrane 36 via gravitational force so that the cells may not be pulled out of the cell culture vessel 10 during the perfusion process.

Once the cells have settled, at block 94, perfusion of the cells within the cavity 16 of the cell culture vessel 10 may be performed by simultaneously adding fresh medium 68 through the feeding port 50 in the vessel body 14 as spent or used medium 68 is removed via the drain port 52. As previously discussed, the perfusion may be filter-free, such that there is not a physical blockage within the drain port 52 for blocking the cells from entering the drain port 52 when the drain port 52 is used for media removal. However, the slanting angle, the position, diameter, and fluid removal rate out of the drain port 52 permits removal of the medium 68 without removing any significant quantities of cells. The drain port 52 may be disposed such that it is fully or partially submerged under the surface of the medium 68 within the cell culture vessel 10. In some embodiments, the drain port 52 may reach to the cell expansion surface (e.g., the membrane 36). Further, the diameter of the opening of the drain port 52 may be sized such that an inhaling velocity through the drain port 52 used to pull the media out of the cavity 16 may create a suction force on individual cells adjacent to the drain port 52 that is lower than the gravitational force pulling the cells toward the membrane 36. As such, when the cell culture vessel 10 is in a static, planar position during perfusion, the drain port 52 permits removal of the used medium 68 without removal of the growing cell culture. Further, upon removal of the used medium 68, impurities and growth-inhibitory byproducts of the cell expansion may be removed as well. Therefore, the drain port 52 may serve as a media removal port and an impurity removal port.

Figure 5:
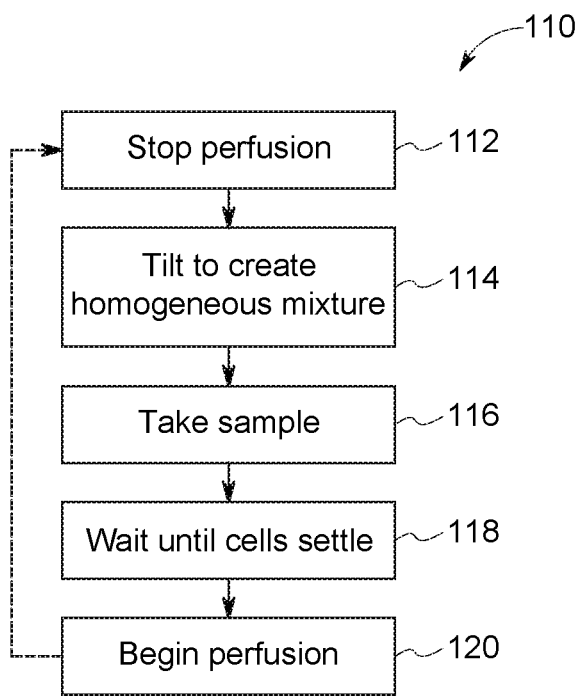
FIG. 5 is a flow diagram of an embodiment of a method of online cell sampling using the cell culture vessel of FIG. 1, in accordance with aspects of the present disclosure.

In some embodiments, during the cell expansion process, at block 96, one or more online homogeneous sample may be taken of the cell culture from the cell culture vessel 10 for monitoring the cell expansion throughout the culture period, as discussed in greater detail with reference to FIG. 5. With proper agitation, the rigid structure of the cell culture vessel 10 facilitates homogeneity of the samples. At block 98, the perfusion, including the simultaneous, or near simultaneous, adding and removing of the medium 68, may be continued until a second higher cell density, or a preferred cell density, is reached. Once the preferred cell density is reached through the perfusion process, at block 100, the cells within the cell culture vessel 10 may be harvested via the drain port, or other method. The cell culture vessel 10 may support high cell density expansion through the filter-free perfusion in a compact structure, and facilitates a perfusion-based washing of the cells and impurity removal such that the cells may not need to be further washed in a designated cell washing device after the cells have been harvested from the cell culture vessel 10.

To monitor cell growth and to determine whether the cell density within the cell culture vessel 10 has reached, one or more online samples may be taken from the cell culture vessel 10. FIG. 5 a flow chart of a method 110 for taking an online sample of the cell culture from the cell culture vessel 10 to monitor cell growth during the culture period. As the online sample may be taken while perfusion is being performed for cell expansion, at block 112, the perfusion (e.g., the simultaneous adding and removing of medium 68 from the cavity 16 of the cell culture vessel 10) may be stopped. Next, to create a homogeneous mixture, at block 114, the cell culture vessel 10 may be tilted or oscillated. The tilting or oscillating of the cell culture vessel 10 may be about a horizontal axis, or axes, of the vessel body 14 or the cell culture vessel 10. The rigid structure of the cell culture vessel 10, including the bottom plate 12 and the vessel body 14, in conjunction with the tilting of the vessel facilitates generation of a wave within the cavity 16 to mix the cell culture with only a small motion. Such tilting or oscillation may cause the cells on the membrane 36 to be suspended in the medium 68 so that the sample taken may more accurately reflect the cell density within the cell culture vessel 10.

Next, at block 116, the sample may be taken via the drain port 52. As previously discussed, the drain port 52 may serve as a dual function port, enabling removal of the spent medium 68, including impurities, and removal of cells.

Once the online sample has been taken, at block 118, there may be a waiting period where the cell culture vessel 10 is placed in a static, planar position to enable the cells to settle back down to the membrane 26 (e.g., cell expansion surface). Settling of the cells within the cell culture vessel 10 before perfusion is started again may prevent the cells from being removed through the drain port 52 when perfusion begins again, as the drain port 52 may not reach to the membrane 36. In some embodiments, positioning of the drain port 52 closer to the surface of the medium 68 within the cavity 16 than to the membrane 36 may decrease the time that it takes for the cells to settle below the drain port 52, which may therefore minimize the impact of the method 110 on the perfusion process. The time that it takes for cells to settle below the drain port 52 may further be reduced by the low-profile structure of the cell culture vessel providing for a lower overall media height. After the cells have settled, at block 120, the perfusion process may begin again. The method 110 for taking online samples may be repeated throughout the perfusion cell expansion process until the preferred cell density is reached. It should be understood that the methods 90 and 110 may be performed together to reach the preferred high density cell culture using the cell culture vessel 10.

In some embodiments, the cell culture vessel 10 may further be used to concentrate the cell culture within the same vessel. To concentrate the cell culture, the medium 68 may continue to be pulled out via the drain port 52, but the addition of new media via the feeding port 50 may be stopped or reduced in flow rate relative to the rate the medium is being removed from the drain port. Thus, the cell culture within the cell culture vessel 10 may have a smaller volume for the same density of cells, thus concentrating the cell culture. Concentration of the cell culture using the cell culture vessel 10, which was also used for cell expansion, may increase the efficiency of recovery and storage of the cells during the cell manufacturing process. In some embodiments, the cell culture vessel 10 may further be used for other steps in the cell manufacturing process, such as activation.

Figure 6:
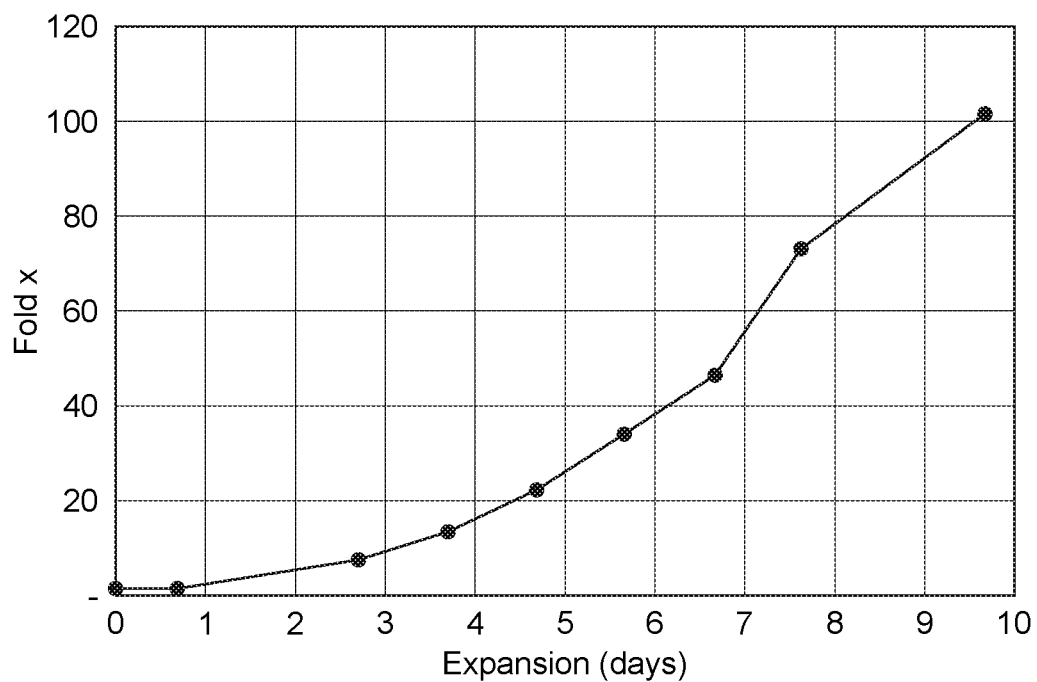
FIG. 6 illustrates a cell growth curve of cell expansion using the cell culture vessel of FIG. 1, in accordance with aspects of the present disclosure.
Figure 7:
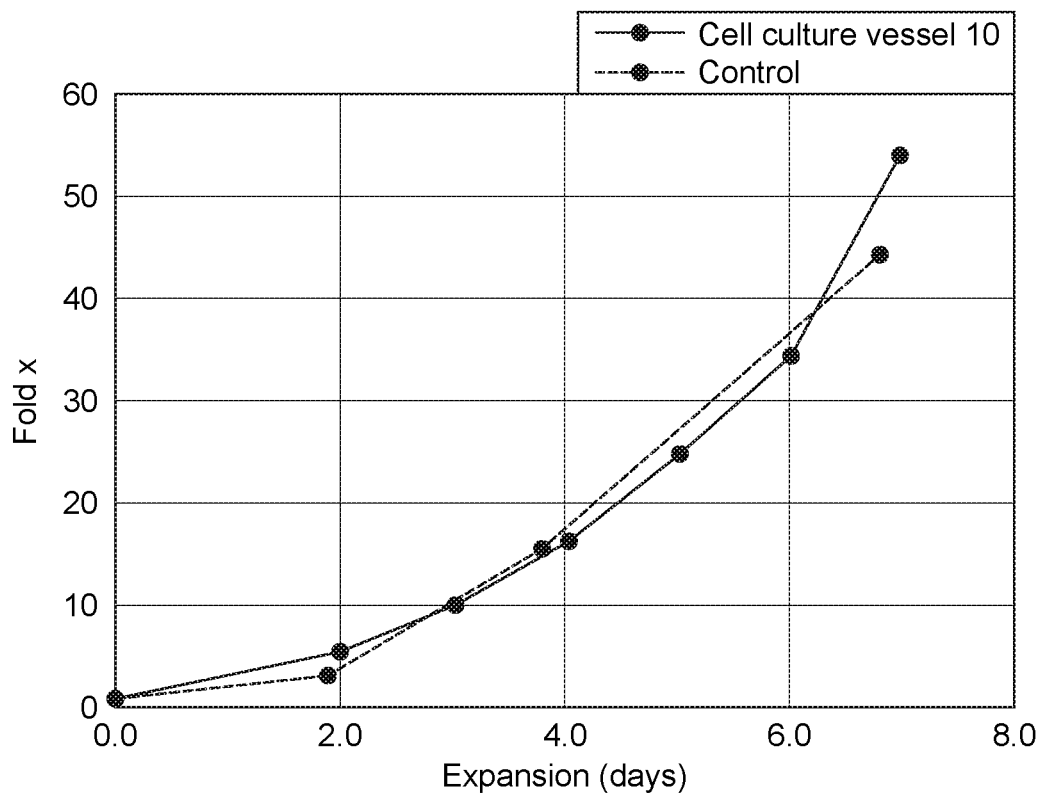
FIG. 7 illustrates a cell growth curve of cell expansion using the cell culture vessel of FIG. 1 compared to a control, in accordance with aspects of the present disclosure.

The cell culture vessel 10 may be a low-profile, compact vessel that may support an increased cell density through cell expansion via filter-free perfusion, as illustrated by FIGS. 6 and 7. FIG. 6 illustrates a cell growth curve of cell expansion using the cell culture vessel 10, while FIG. 7 illustrates the cell growth curve of cell expansion using the cell culture vessel 10 compared to a control. As shown, in a 7-day cell expansion using a control and a 7-day cell expansion using the cell culture vessel 10 and the method 110, the cell culture vessel 10 generated a cell culture with an increased cell density after the culture period compared to the control, both starting with the same activated seed cells. The cell culture vessel 10 is designed to facilitate homogeneous mixing using pre-defined tilting motion, e.g., 1.1 Hz oscillation at +/−2 degrees of tilting angle for 5 minutes. This feature allows for homogeneous sampling of the culture.

Technical effects of the disclosure include a low-profile, compact, static cell culture vessel that may utilize perfusion to support high density cell expansion. The position of the ports used for the addition of new media and the removal of used media reduces the media height within the cell culture vessel. The low media height in turns leads to compact configurations of the structure of the cell culture vessel while still supporting high density cell culture. Further, the removal of use media during the perfusion process acts to remove impurities in the cell culture vessel. As such, the cell culture vessel may reduce the use of a separate designated cell washing device for removing impurities after the cell culture is harvested, thus, increasing the efficiency of the cell expansion process. Further, the filter-free drain port of the cell expansion vessel may be a dual functionality port enabling used media removal, as well as cell removal via a single port. The position and diameter of the drain port permit the used media to be removed without removing the cells during the perfusion process; however, the position of the drain port relative to the cell expansion surface within the cell culture vessel and the angled side of the cell culture vessel on the side having the drain port may, when desired, permit removal of the cells for online sampling of the cell culture for monitoring cell growth throughout the culture period. Further, the cell culture vessel may be used to concentrate the cell culture, which may increase efficiency of the recovery and storage of the cells after expansion and harvesting.

This written description uses examples as part of the disclosure, including the best mode, and also to enable any person skilled in the art to practice the invention, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
introducing a suspension comprising cells suspended in a cell culture medium through at least a feed port or a drain port into a cavity of a cell culture vessel, the suspension being in an amount sufficient to cover a gas permeable, liquid impermeable membrane positioned at a bottom of the cell culture vessel, the feed port configured to permit additional cell culture, medium into the cavity, and the drain port configured to permit removal of the cells, cell culture medium, and used cell culture medium from the cavity;
allowing the cells to settle on the gas permeable, liquid impermeable membrane by gavity;
perfusing the cells with the cell culture medium, wherein the perfusing comprises
removing the used cell culture medium through the drain port and introducing the additional cell culture medium through the feed port such that a constant volume is maintained in the cell culture vessel until the cells expand to a desired density, wherein the removing and introducing are performed subsequent to allowing the cells to settle on the gas permeable, liquid impermeable membrane;

resuspending the cells in the cell culture medium in the cell culture vessel, wherein the resuspending is performed after the desired cell density is attained; and removing the resuspended cells and the cell culture medium through the drain port.

2. The method of claim 1, wherein removing the used cell culture medium comprises removing impurities, cell culture byproducts, or a combination thereof from within the cell culture vessel.

3. The method of claim 1, wherein the allowing the cells to settle to the gas permeable, liquid impermeable membrane, the removing the used cell culture medium, and the introducing the additional cell culture medium comprise positioning the cell culture vessel such that the gas permeable, liquid impermeable membrane is level to allow even distribution of cells.

4. The method of claim 1, wherein the resuspending of the cells in the cell culture medium comprises oscillating the cell culture vessel through a defined angle for a period of time.

5. The method of claim 1, comprising sampling a homogeneous mixture of the cells within the cell culture vessel via the drain port to monitor cell growth, wherein the drain port is a filter-free port disposed through a wall of the cell culture vessel at a position at least partially below a surface of the cell culture medium within the cell culture vessel and at or above the gas permeable, liquid impermeable membrane, and wherein the sampling comprises tilting the cell culture vessel toward the drain port.

6. The method of claim 1, wherein the removing of the resuspended cells and the cell culture medium through the drain port comprises tilting the cell culture vessel to minimize a hold-up volume.

7. The method of claim 1, wherein the cell culture medium within the cell culture vessel extends from the gas permeable, liquid impermeable membrane to a height within a range of 0.3 cm to 2 cm of medium.

8. The method of claim 1, wherein a ratio of cell culture medium volume per surface area of the gas permeable, liquid impermeable membrane is below a threshold value.

9. The method of claim 1, wherein a headroom space above the cell culture medium within the cell culture vessel has a height that is approximately equal to a height of the cell culture medium relative to the gas permeable, liquid impermeable membrane.

10. A method, comprising:
introducing a suspension comprising cells suspended in a cell culture medium through at least a feed port or a drain port into a cavity of a cell culture vessel, the suspension being in an amount sufficient to cover a gas permeable, liquid impermeable membrane positioned at a bottom of the cell culture vessel, the feed port being disposed through a surface of the cell culture vessel and configured to permit additional cell culture medium into the cavity, and the drain port being disposed through a surface of the cell culture vessel and configured to permit removal of the cells, cell culture medium, and used cell culture medium from the cavity;

allowing the cells to settle on the gas permeable, liquid impermeable membrane by gravity;

perfusing the cells with the cell culture medium, wherein the perfusing comprises introducing the additional cell culture medium through the feed port while simultaneously or nearly simultaneously removing the used cell culture medium from the cell culture vessel via the drain port to maintaining a constant volume within the cell culture vessel until the cells expand to a desired cell density, wherein the perfusing is performed subsequent to allowing the cells to settle on the gas permeable, liquid impermeable membrane;

sampling the cells via the drain port to determine whether the desired cell density is reached;

repeating, upon determining that the desired cell density has not been reached, the perfusing of the cells until the desired cell density is reached;

resuspending the cells in the cell culture medium in the cell culture vessel, wherein the resuspending is performed after the desired cell density is reached; and removing the resuspended cells and the cell culture medium through the drain port.

11. The method of claim 10, wherein the sampling comprises:
stopping the perfusing of the cells;
resuspending the cells in the cell culture medium;
removing a homogeneous sample of the resuspended cells via the drain port determine whether the desired cell density has been reached; and
waiting, upon determining that the desired cell density has not been reached, for a waiting period for the cells to settle to the gas permeable, liquid impermeable membrane, wherein the perfusing is not initiated until the cells have sufficiently settled at or beneath the drain port.

12. The method of claim 11, wherein resuspending the cells in the cell culture medium comprises oscillating the cell culture vessel about one or more horizontal axis of the cell culture vessel to generate a wave within the cavity of the cell culture vessel to create a homogenous mixture of the cells and the additional cell culture medium, wherein the cell culture vessel comprises a structure with sufficient headspace configured to facilitate generation of the wave.

13. The method of claim 10, wherein the drain port is, a filter-free port disposed through a wall of the cell culture vessel at a position at least partially below a surface of the cell culture medium within the cell culture vessel and at or above the gas permeable, liquid impermeable membrane.

14. The method of claim 10, wherein the drain port is sized such that an inhaling velocity used to remove the used cell culture medium via the drain port creates a suction force on the cells within the cell culture vessel that is less than a gravitational force pulling the cells to the gas permeable, liquid impermeable membrane.

15. The method of claim 10, comprising concentrating the suspension of cells of the desired cell density such that the suspension of cells of the desired cell density comprises a smaller volume, wherein the concentrating comprises discontinuing the introduction of additional cell culture medium via the feeding port and continuing the removing of the used cell culture medium via the drain port, and wherein the removing of the cells comprises removing the concentrated cells.

16. The method of claim 10, wherein a ratio of cell culture medium volume per surface area of the gas permeable, liquid impermeable membrane is below a threshold value.

* * * * *

UNITED STATES PATENT AND TRADEMARK OFFICE
CERTIFICATE OF CORRECTION

PATENT NO. : 10,889,792 B2
APPLICATION NO. : 15/893336
DATED : January 12, 2021
INVENTOR(S) : Weston Blaine Griffin et al.

Page 1 of 1

It is certified that error appears in the above-identified patent and that said Letters Patent is hereby corrected as shown below:

In the Claims

At Column 12, Line 63, Claim 1, delete "gavity" and insert --gravity--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*